United States Patent [19]

Jaxa-Chamiec et al.

[11] Patent Number: 5,273,740
[45] Date of Patent: Dec. 28, 1993

[54] POLYSTYRENE ANION EXCHANGE POLYMERS

[75] Inventors: Albert A. Jaxa-Chamiec, Rickmansworth; Deirdre M. B. Hickey; Virendra P. Shah, both of Welwyn, all of England

[73] Assignee: SmithKline & French Laboratories Limited, Welwyn Garden City, England

[21] Appl. No.: 526,346

[22] Filed: May 21, 1990

[30] Foreign Application Priority Data

May 22, 1989 [GB] United Kingdom ........ 8911719

[51] Int. Cl.$^5$ ............ A61K 31/785; C08F 8/44; C08F 12/08
[52] U.S. Cl. .................... 424/78.01; 521/32; 525/333.6; 526/263
[58] Field of Search ......... 525/333.6, 327.1, 326.9, 525/332.2; 526/263; 521/32, 33, 38; 424/78.01

[56] References Cited

U.S. PATENT DOCUMENTS

| | | | |
|---|---|---|---|
| 3,787,474 | 1/1974 | Daniels et al. | 424/78 |
| 3,989,088 | 8/1975 | Cohen et al. | 96/84 |
| 4,198,395 | 4/1980 | De Simone | 424/79 |
| 4,311,799 | 1/1982 | Miyake et al. | 521/31 |
| 4,510,128 | 4/1985 | Khanna | 424/79 |
| 4,532,128 | 7/1985 | Sheldon et al. | 424/78 |
| 4,721,666 | 1/1988 | Yamanouchi et al. | 430/213 |
| 4,798,870 | 1/1989 | Lyle, Jr. et al. | 525/333.3 |
| 4,826,924 | 5/1989 | Koural et al. | 525/331.3 |

FOREIGN PATENT DOCUMENTS 929391  6/1963  United Kingdom.
1286949 12/1969 United Kingdom.
2026501-A 2/1980 United Kingdom.

OTHER PUBLICATIONS

Sugh et al. *Reactive Polymers* 8 (1988) 3–6.
Haratake et al. *Analytical Sciences* 4 (Dec. 1988) 591–594.
Walfish, et al., Water, Air & Soil Pollution 12:477–484.
Carpov, et al., J. Macromol. Sci. Chem., A22(5-7):9-07-929 (1985).
Takeuchi, et al., Chem. Pharm. Bull. 32(3):823–831 (1984).
Petrariu, et al., Revue Roumaine de Chimie, 25:145–154 (1980).
Wessling, et al., Makromol. Chem., suppl. 10/11:319-333 (1985).

Primary Examiner—Paul R. Michl
Assistant Examiner—Tae H. Yoon
Attorney, Agent, or Firm—Wayne J. Dustman; Stephen Venetianer; Edward T. Lentz

[57] ABSTRACT

Polystyrene polymers bearing a quaternary ammonium group are disclosed. They are useful in the treatment of hypercholesterolaemia and the prevention of atherosclerosis. A compound of the invention is 6-(N,N-dimethyl-N-octylammonio)hexanoylated polystyrene chloride.

12 Claims, No Drawings

POLYSTYRENE ANION EXCHANGE POLYMERS

The present invention relates to novel polystyrene anion exchange polymers, processes for their preparation, intermediates useful in their preparation, pharmaceutical compositions containing them and their use in the lowering of plasma cholesterol levels in humans.

Coronary Heart Disease (CHD) is one of the most serious health problems of contemporary society. Worldwide epidemiological studies have shown that the incidence of CHD is related to a number of independent risk factors, in particular, for example, high concentrations of serum cholesterol (hypercholesterolaemia). Such adverse factors lead to atherosclerosis, and ultimately, in severe cases, intermittent claudication, cerebrovascular insufficiency, thrombosis and cardiac arrest.

It is known that ion exchange polymers, in particular polystyrene polymers can be used as sequestering agents to bind non-absorbed bile acids and salts in the intestinal tract, forming complexes which are then excreted in the feces. This sequestering leads to a decrease in the amount of bile acids returning to the liver via enterohepatic circulation. The synthesis of replacement bile acids from hepatic cholesterol depletes hepatic cholesterol, regulates hepatic LDL receptors and consequently reduces plasma cholesterol levels. Such sequestering polymers have been recognized as useful for the treatment of hypercholesterolaemia, and it is now proven that reducing serum cholesterol with bile acid sequestrants has a beneficial effect on protecting against the occurrence of coronary heart disease.

The polystyrene polymers known in the art to have such sequestering activity are, in general, those bearing a di- or tri-loweralkyl ammonium group, such as a trimethylammonium group. For example, GB 1286949 discloses a series of macroporous polystyrene polymers having 5-20% cross-link, and GB 1579490 discloses a series of microporous polymers having 8-20% cross-link. In addition, GB 2026501discloses a series of, inter alia, polystyrene polymers which are said to have particular water absorption capacities, i.e. 69-73% by weight of polmer weight. In each of the foregoing, the polystyrene polymers bear di- or tri-loweralkyl ammonium groups, in particular a trimethylammonium group.

One particular agent based on a polystyrene polymer which is currently used to lower serum cholesterol levels in humans by binding bile acids in the intestinal tract is cholestyramine (GB 92939). Cholestyramine is a crosslinked anion exchange polystyrene polymer bearing ionized trimethylammonium group bound to the polymer backbone. However, the use of this agent is associated with a number of undesirable side-effects, for example, it is unpalatable and must be taken in large doses (up to 36 g per day) and causes, in some cases, bloating, constipation and other gut side-effects. In addition, its ability to bind bile acids is inefficient with respect to the amounts of polymer which it is necessary to use. It is the object of the present invention to provide compounds which overcome the advantages of known sequestering agents.

The present invention therefore provides in a first aspect, polystyrene polymers of structure (I):

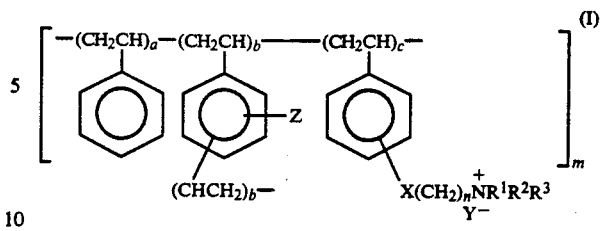

in which
X is $CH_2$, CO or CHOH;
Z is H or a group $X(CH_2)_nN^+R^1R^2R^3$;
n is 1 to 20;
$R^1$ and $R^2$ are the same or different and are each $C_{1-4}$alkyl;
$R^3$ is $C_{1-20}$alkyl; or $R^1$, $R^2$ and $R^3$ together with the nitrogen atom to which they are attached form a ring, optionally containing one or more further heteroatoms, and optionally being substituted with a $C_{1-4}$alkyl group;
a, b and c are numbers which indicate the relative molar percentages of the units present in a random distribution in said polymer, (b) being from about 0.5 to about 10 molar percent, and (c) being from about 30 to about 99 molar percent;
m is a number indicating the degree of polymerisation of said polymer, and
$Y^-$ is a physiologically acceptable counter ion.

Suitably X is $CH_2$, CO or CHOH; preferably X is $CH_2$ or CO; most preferably X is $CH_2$.

Suitably n is 1 to 20; preferably n is 1 to 10; most preferably n is 5 to 10.

Suitably $R^1$ to $R^3$ together with the nitrogen atom to which they are attached form a ring, optionally containing one or more further heteroatoms and optionally being substituted by a $C_{1-4}$alkyl group.

Suitable rings include 5 and 6 membered carbocyclic rings, optionally containing one or more further nitrogen, oxygen or sulphur atoms, for example, imidazolyl, N-methylimidazolyl, morpholino and N-methylmorpholino groups.

More suitably the groups $R^1$ and $R^2$ are the same or different and are each $C_{1-4}$alkyl and $R^3$ is $C_{1-20}$ alkyl; preferably $R^1$ and $R^2$ are the same; most preferably $R^1$ and $R^2$ are both methyl; preferably $R^3$ is $C_{1-12}$ alkyl.

Suitably (b) is from about 0.5 to about 10 molar percent of said polymer, preferably (b) is from about 1 to about 8 molar percent of said polymer; most preferably from about 1 to about 4 molar percent.

Suitably $Y^-$ is a physiologically acceptable counter ion such as a sulphate, bicarbonate, carbonate, formate, acetate, sulphonate, propionate, malonate, succinate, malate, tartrate, citrate, maleate, fumarate, ascorbate, glucuronate, phosphate, or halide, or the anion of an amino acid such as aspartic or glutamic acid. More suitably $Y^-$ is a phosphate, sulphate or a halide ion; preferably a halide ion, in particular chloride.

m is a number indicating the degree of polymerisation of said polymer. Owing to the three dimensional cross-linkage precise figures cannot be given for m, but in any case will be greater than 1000.

The polystyrene polymers of the present invention are also characterized by their total exchange capacity i.e. the theoretical maximum capacity of the polymer if each counter ion were to be exchanged with bile acid. In this specification the total exchange capacity is defined in terms of the number of milliequivalents of counter ion per gram of dry weight of polymer.

Suitable total exchange capacities are in the range of, for example where the counter ion $Y^-$ is a halide ion such as chlorine, from 1.5 to 4.5 meq $Cl^-$ per gram of polymer. Preferred within this range are polymers having a total exchange capacity of between 1.5 and 3 meq $Cl^-$/gram of polymer.

In addition, it is to be noted that the approximate molar percentages (a), (b) and (c) are calculated from the monomer mixture or, in some instances (c) from microanalytical data.

It is to be noted that the term 'bile acid' when used herein shall be taken to include bile acids, bile salts and conjugates thereof.

The polystyrene polymers of the present invention can be prepared by processes analogous to those known in the art, for example, the polystyrene polymers of structure (I) can be prepared by reaction of a polymer of structure (II)

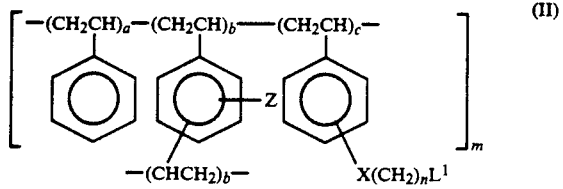
(II)

in which X, Z, n, a, b, c and m are as described for structure (I) and $L^1$ is a group displaceable by an amine, with an amine of structure $R^1R^2R^3N$ (III) in which $R^1$ to $R^3$ are as described for structure (I), or (b) for polymers of structure (I) in which $R^7$ is $C_{1-20}$alkyl; reaction of a polymer of structure (IV)

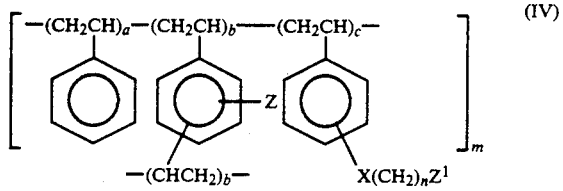
(IV)

in which Z, X, n, a, b, c and m are as described for structure (I) and $Z^1$ is $NR^1R^2$ or $NR^2R^3$ in which $R^1$ to $R^3$ are as described for structure (I) with a compound of structure $R^4Y$ (V) in which $R^4$ is a $C_{1-4}$alkyl group when $Z^1$ is $NR^2R^3$ or $R^4$ is a $C_{1-20}$alkyl group when $Z^1$ is $NR^1R^2$, and Y is a group displaceable by an amine.

Groups $L^1$ displaceable by an amine include, for example, halogen atoms, in particular, bromine. Others will be apparent to those skilled in the art and include, for example, chlorine, iodine, tosylate and mesylate etc.

The reaction between a polymer of structure (II) and an amine of structure (III) can be carried out in a suitable solvent at elevated temperature. Suitable solvents include for example, a $C_{1-4}$alkanol, N-methylsolvent pyrrolidone, sulpholane, dimethylformamide, nitromethane or tetrahydrofuran. Preferably the reaction is carried out in dimethylformamide or N-methylpyrrolidone at a temperature of between about 50° and 80° for up to 24 hours or until the reaction is complete.

The reaction between a polymer of structure (IV) and a compound of structure (V) can be carried out in a suitable inert solvent such as a $C_{1-4}$alkanol, nitromethane, sulpholane, N-methylpyrrolidone, dimethylformamide or tetrahydrofuran at elevated temperature.

The intermediate polymers of structure (II) can be prepared from readily available materials by methods known to those skilled in the art. For example, compounds of structure (II) in which X is CO and $L^1$ is bromine can be prepared from reaction of polystyrene with a compound of structure (VI)

(VI)

in which $L^1$ and n are as described for structure (II) and $L^2$ is a suitable leaving group.

Leaving groups $L^2$ include for example halogen atoms, in particular chlorine, others will be apparent to those skilled in the art and include for example bromine.

The reaction between polystyrene and compounds of structure (VI) can be carried out in a suitable solvent, such as dichloromethane, in the presence of an acid, in particular a Lewis acid, such as aluminum trichloride at a temperature of between ambient and reflux temperature of the solvent used.

Other polymers of structure (II) in which X is other than CO can be prepared from the above compounds in which X is CO. For example, polymers of structure (II) in which X is $CH_2$ and $L^1$ is bromine can be prepared from compounds of structure (II) in which X is CO and $L^1$ is bromine by reduction with a suitable reducing agent, for example, triethyl tin hydride; and polymers of structure (II) in which X is CHOH and $L^1$ is bromine by reduction with a reducing agent such as sodium borohydride, in a suitable solvent such as IMS.

Compounds of structure (VI) are available commercially or can be prepared from commercially available precursors by methods known in the art. For example, the compound of structure (VI) in which $L^1$ is bromine and $L^2$ is chlorine and n is 10 can be prepared by reaction of thionyl chloride with 11-bromoundecanoic acid.

The intermediate polymers of structure (IV) can be prepared from polymers of structure (II) by reaction with an amine of structure $R_2NH$ in which $R_2$ is $R^1R^2$ or $R^2R^3$ under the same or analogous conditions to those indicated for the reaction between a polymer of structure (II) and (III).

In addition, polymers of structure (I), (II) and (IV) can be prepared by polymerisation of suitable monomer mixtures under standard polymerisation conditions. For example, polymerisation can be carried out in an aqueous suspension comprising, for example, polyvinyl alcohol in the presence of an initiator at elevated temperature. Suitable initiators include, for example, AIBN.

The polystyrene polymers of structure (I) have been found to bind bile acids in vitro experiments and in in vivo animal models they have been found to increase the amount of bile acids detectable in the feces. In particular, when compared to the known sequestrants e.g. cholestyramine, the polymers of structure (I) have surprisingly been found to have an unexpected profile of activity which is thought will provide advantages over the known compounds in the lowering of serum cholesterol levels in animals, in particular humans. More specifically, in in vitro experiments, when compared to cholestyramine the compounds of structure (I) have been found to bind comparable amounts of bile acid per gram of polymer (at physiological concentrations of bile acids), and to bind the bile acid more strongly i.e., the bile acids have been found to dissociate more slowly from the compounds of the invention. It is expected that compounds having such qualities will be able to achieve significant lowering of plasma cholesterol levels at much lower dosages than has hitherto been possible with known sequestrants (currently given at up to 36 g/day).

As indicated earlier it is recognized that removal of bile acids from the intestinal tract in this way lowers serum cholesterol levels and also has a beneficial effect on protecting against atherosclerosis and its dependent clinical conditions. The present invention therefore provides in a further aspect, polystyrene polymers of structure (I) for use in therapy, in particular for the lowering of serum cholesterol levels in mammals, including humans. In addition the polymers of structure (I) are expected to be of use in protecting against atherosclerosis and its sequelae, and for example in the treatment of pruritus and diarrhoea.

In view of the foregoing the present invention also provides a method of lowering serum cholesterol levels in mammals which comprises administering to a mammal in need thereof an effective serum cholesterol lowering amount of a polystyrene polymer of structure (I); and a method of protecting against atherosclerosis.

When used in therapy the polystyrene polymers of structure (I) are in general administered in a pharmaceutical composition.

In a still further aspect of the present invention there is therefore provided a pharmaceutical composition comprising a polystyrene polymer of structure (I) in association with a pharmaceutically acceptable carrier.

The compositions of the present invention can be prepared by techniques well known to those skilled in the art of pharmacy and include all those known for the formulation of polystyrene polymers for human use.

The polymers are preferably administered as formulations in admixture with one or more conventional pharmaceutical excipients which are physically and chemically compatible with the polymer, which are nontoxic, are without deleterious side-effects but which confer appropriate properties on the dosage form.

In general, for liquid formulations, aqueous based pharmaceutically acceptable carriers such as water itself or aqueous dilute ethanol, propylene glycol, polyethylene glycol or glycerol or sorbitol solutions are preferred.

Such formulations can also include preservatives an flavoring and sweetening agents such as sucrose, fructose, invert sugar, cocoa, citric acid, ascorbic acid, fruit juices etc. In general, digestible oil or fat based carriers should be avoided or minimized as they contribute to the condition sought to be alleviated by use of the polymers. They are also subject to absorption by the polymers during prolonged contact, thus reducing the capacity of the polymer to absorb bile acids after administration.

The polymers can also be prepared as 'concentrates', for dilution prior to administration, and as formulations suitable for direct oral administration. They can be administered orally ad libitum. On a relatively continuous basis for example by dispersing the polymer in drinks or food.

Preferably, the polymers are administered in tablet form or in gelatin capsules containing solid particulate polymer or a non-aqueous suspension of solid polymer containing a suitable suspending agent. Suitable excipients for such formulations will be apparent to those skilled in the art and include, for example, for tablets and capsules lactose, microcrystalline cellulose, magnesium stearate, povidone, sodium starch glycollate and starches; and for suspensions in capsules, polyethylene glycol, propylene glycol and colloidal silicon dioxide.

Preferably the polymer is administered in unit dosage form, each dosage unit containing preferably from 0.5 g to 1.5 g of polymer.

The daily dosage regimen for an adult patient may be, for example, a total daily oral dose of between 1 and 10 g, preferably 1-5 g, the compound being administered 1 to 4 times a day depending on the size of individual dosage units. Suitably the compound is administered for a period of continuous therapy of one month or more sufficient to achieve the required reduction in serum cholesterol levels.

In addition the polymers of the present invention can be co-administered (together or sequentially) with further active ingredients such as HMGCoA reductase inhibitors and other hypocholesterolaemic agents, and other drugs for the treatment of cardiovascular diseases.

The following data and examples indicate the properties and preparation of the polymers of the present invention. Temperatures are recorded in degrees celsius. The exchange capacity of the substituted polymers was determined by elemental analysis and/or potentiometric titration of chloride ion. figures quoted are expressed as milliequivalents of exchangeable chloride ion per gram of dry polymer weight.

The polystyrene beads used were a commercial product (Bio-Rad SX-1) 1% cross-linked with divinylbenzene of bead size 50–100$\mu$. Values of the molar fractions a, b, c can be calculated and were approximately 0.26:0.01:0.73 for Examples 1-8 and 13-18 and approximately 0.51:0.01:0.43 for Examples 9-12 inclusive.

EXAMPLE 1

(a) To a suspension of puriss aluminum trichloride (32.0 g) in dry dichloromethane (300 ml), 6-bromohexanoyl chloride (53.4 g) was added and the mixture stirred at room temperature for 20 minutes. The resulting solution was filtered and the filtrate added to a suspension of 1% cross-linked polystyrene beads (25.0 g) in 200 ml of dry dichloromethane. The mixture was stirred at room temperature for 28 hours. The polymer Was filtered off, washed With water, methanol and finally with diethyl ether, then dried at 67° in vacuo for 48 hours to give 6-bromohexanoylated polystyrene as off white resin beads (53.9 g) (3.13 meq Br/g of resin).

(b) 33% Trimethylamine in industrial methylated spirit (IMS) (100 ml) was added to a suspension of the above polymer (10 g) in N,N-dimethylformamide (DMF) (200 ml). The mixture was stirred at 66° for 18 hours. The polymer was filtered off, washed with methanol, aqueous 2N sodium hydroxide, aqueous 2N hydrochloric acid, water, methanol and finally with diethyl ether to give 6-(trimethylammonio)hexanoylated polystyrene chloride as off white polymer beads (10.35 g) (2.94 meq Cl$^-$/g).

EXAMPLE 2

The polymer prepared in Example 1a (6.5 g) was added to pyridine (100 ml) and the mixture stirred at reflux temperature for 18 hours. The polymer was filtered off, washed as in Example 1b, and dried at 90° in vacuo to give 6-(1-pyridinio)hexanoylated polystyrene chloride (7.1 g) (2.81 meq Cl$^-$/g)

EXAMPLE 3

To a suspension of the polymer prepared in Example 1a (10.0 g) in DMF (200 ml), N,N-dimethyloctylamine (15.3 g) was added and the mixture was heated at 60° for 18 hours. The polymer was filtered off and washed as in Example 1b, and dried at 62° in vacuo to give 6-(N,N-dimethyl-N-octylammonio)hexanoylated polystyrene chloride (12.5 g) (2.24 meq Cl$^-$/g).

EXAMPLE 4

The polymer prepared in Example 1a (10 g) was treated with N,N-dimethyldodecylamine (33.0 g) as in Example 3 to give 6-(N,N-dimethyl-N-dodecylammonio)hexanoylated polystyrene chloride (14.5 g), (2.06 meq Cl$^-$/g).

EXAMPLE 5

(a) 11-Bromoundecanoic acid (400 g) was added to thionyl chloride (600 ml) and the solution heated at 80° for 0.5 hour. The thionyl chloride was distilled off and the dark oily residue distilled in vacuo to give 11-bromoundecanoyl chloride, b.p. 144°, 0.7 mm Hg, (346.8 g, 81%).

(b) The above acylchloride (b 114.0 g) was added to a suspension of puriss aluminum trichloride (48.0 g) in dry dichloromethane (300 ml) and stirred at room temperature for 20 minutes. The solution was filtered and the filtrate added to a suspension of % cross-linked polystyrene beads (30.0 g) in dry dichloromethane (200 ml) and the mixture stirred for 24 hours at room temperature. The polymer was filtered off, washed with water, industrial methylated spirit (IMS) and finally with diethyl ether, and dried at 50° in vacuo at give 11-bromoundecanoylated polystyrene as light brown solid (111.0 g) (2.51mg Br/g).

(c) A 33% solution of trimethyaamine in IMS was added to a suspension of the above polymer (20 g) in DMF (50 ml) and the mixture heated at 60° for 18 hours. The polymer was filtered off, washed as in Example 1b, and dried at 50° in vacuo to give 11-(trimethylammonio)undecanoylated polystyrene chloride as light brown beads (20.02 g) (2.32 meq Cl$^-$/g).

EXAMPLE 6

The 11-bromoundecanoylated polystyrene prepared in Example 5b (20 g) was treated with N,N-dimethyloctylamine (42.7 g) in DMF (200 ml) to give, after work-up as described in Example 2b, 11-(N,N-dimethyl-N-octylammonio) undecanoylated polystyrene chloride (24.76 g) (1.88 meq Cl$^-$/g).

EXAMPLE 7

(a) 11-Bromoundecanoylated polystyrene (145.7 g) (2.58 meq Br/g) was prepared from polystyrene beads (50 g) and 11-bromoundecanoyl chloride (171.6 g) as described in Example 5a.

(b) To a suspension of this polymer (50 g) in DMF (400 ml), N,N-dimethyldodecylamine (80.9 g) was added and the mixture heated at 60° for 22 hours. After washing as in Example 1b, 11-(N,N-dimethyl-N-dodecylammonio)undecanoylated polystyrene chloride was obtained as offwhite polymer beads (65.7 g) (1.77 meq Cl$^-$/g).

EXAMPLE 8

11-Bromoundecanoylated polystyrene (Example 7a) (5 g) was treated with N-methylimidazole (8.3 g) in DMF (50 ml) at 60° for 22 hours. After work-up as described in Example 1b, 11-(3-methylimidazolyl)-undecanoylated polystyrene chloride was isolated is off-white polymer beads (5.14 g) (2.27 meq Cl$^-$/g).

EXAMPLE 9

(a) 11-Bromoundecanoyl chloride (71.0 g) was added to a suspension of puriss aluminum trichloride (16.0 g) in dry dichloromethane (300 ml) and the mixture stirred for 20 minutes. The resultant solution was filtered, the filtrate added to a suspension of 1% cross-linked polystyrene beads (25 g) in dry dichloromethane (200 ml) and the mixture stirred at room temperature for 18 hours. The polymer was filtered off, washed with water, methanol and finally with diethyl ether and dried at 50° in vacuo to give 11-bromoundecanoylated polystyrene as buff colored polymer beads (51.8 g) (2.01 meq Br/g).

(b) The above polymer (10.0 g) was added to DMF (100 ml) and to it 33% trimethylamine in IMS (200 ml) was added. The mixture was stirred at room temperature for 48 hours and then at 60° for 18 hours. The resin was filtered off, washed as in Example 1b, and dried at room temperature in vacuo for 18 hours to give 11-(trimethylammonio)undecanoylated polystyrene chloride (10.14 g) (2.00 meq Cl$^-$/g).

EXAMPLE 10

To a suspension of the polymer prepared in Example 7a (10 g) in DMF (200 ml), N,N-dimethyloctylamine (20 g) was added and the mixture stirred at 60° for 18 hours. The polymer was filtered off, washed as in Example 1b and dried at room temperature in vacuo for 18 hours to give 11-(N,N-dimethyl-N-octylammonio)undecanoylated polystyrene chloride as a light brown polymer beads (11.68 g) (1.64 meq Cl$^-$/g).

EXAMPLE 11

11-(N,N-Dimethyl-N-dodecylammonio)undecanoylated polystyrene chloride was prepared from the polymer in Example 7a (10 g) and N,N-dimethyldodecylamine (21.6 g) in the same manner as Example 10, and was isolated as buff colored polymer beads (12.41 g) (1.42 meq Cl$^-$/g).

EXAMPLE 12

The polymer from Example 7a (10.0 g) was added to pyridine (100 ml) and the mixture refluxed for 18hours. The resin was filtered off, washed as in Example 1b, and dried at 67° in vacuo for 18 hours to give 11-(1-pyridinio)undecanoylated polystyrene chloride as buff colored polymer beads (10.49 g) (1.84 meq Cl$^-$/g).

EXAMPLE 13

(a) 8-Bromooctanoic acid (200 g) was added slowly to thionyl chloride (325 ml). The mixture was stirred at 60° for 1 hour. Excess thionyl chloride distilled off in vacuo. The dark oily residue was distilled to give 8-bromooctanoyl chloride as colorless oil, b.p. 112°-114°/0.1-0.3 mm Hg, (202.38, 93%).

(b) This acid chloride (87.7 g) was added to a suspension of puriss aluminum trichloride (44.0 g) in dry dichloromethane (300 ml) and the mixture was stirred for 20 minutes at room temperature to give a solution. The solution was filtered, added to a suspension of 1% cross-linked polystyrene beads (30 g) in dry dichloromethane (300 ml) and stirred at room temperature for 24 hours. The solid was filtered off washed with IMS, water, IMS and diethylether and dried at 50° in vacuo for 96 hours to give 8-bromooctanoylated polystyrene (86.23 g), (2.62 meq Br/g).

(c) This polymer (10 g) was treated with 33% trimethylamine in IMS (250 ml) at 70° for 24 hours. After washing as in Example 1b the product 8-(trimethylammonio)octanoylated polystyrene chloride was obtained as off-white polymer beads (9.8 g) (2.40 meq Cl−/g).

EXAMPLE 14

(a) 11-Bromoundecanoyl chloride (76.0 g) was added to a suspension of puriss aluminum trichloride (29.35 g) in dry dichloromethane (200 ml). The mixture was stirred for 20 minutes to give a solution which was filtered. The filtrate was added to a suspension of 1% cross-linked polystyrene beads (20.0 g) in dry dichloromethane (200 ml) and the mixture stirred for 24 hours. Triethylsilane (93.14 g) was added and the mixture stirred for 18 hours at room temperature, then at reflux temperature for 4 hours. The solid was filtered off, washed with IMS, water, IMS, and finally with diethyl ether and dried at 50° in vacuo for 48 hours to give 11-bromoundecylated polystyrene as light brown polymer beads (65.1 g) (2.59 meq Br/g).

(b) 33% Trimethylamine in IMS (20ml) was added to a suspension of the above polymer (7.0 g) in DMF (100ml) and the mixture stirred at 80° for 16 hours. After work-up as for Example 1b, 11-(trimethylammonio)undecylated polystyrene chloride was isolated as pale brown polymer beads (6.55 g) (2.30 meq Cl−/g).

EXAMPLE 15

The polymer prepared in Example 14a (6.26 g) was treated with N,N-dimethyloctylamine (10 g) in DMF (100 ml) at 80° for 18 hours, to give, after work-up as in Example 1b, 11-(N,N-dimethyl-N-octylammonio)undecylated polystyrene chloride (7.41 g) as pale-brown polymer beads 1.83 meq Cl−/g).

EXAMPLE 16

11-(N,N-dimethyl-N-dodecylammonio)undecylated polystyrene chloride (20.23 g) (1.63 meq Cl−/g) was prepared as in Example 4 from the polymer in Example 14a (15.0 g) and N,N-dimethyldodecylamine (25.6 g).

EXAMPLE 17

A suspension of 6-trimethylammonio)hexanoylated polystyrene chloride (Example 1b) (1.0 g) in IMS (50 ml) was treated with sodium borohydride (0.17 g) at room temperature. After 1 hour a further 1 g of NaBH$_4$ was added and the mixture stirred for 18 hours. The mixture was then treated with concentrated HCl (5 ml) and the polymer filtered off and washed with water, IMS, and diethyl ether to give 1-hydroxy-6-(trimethylammonio)hexylated polystyrene chloride (0.72 g) as off-white polymer beads (2.79 meq Cl−/g).

EXAMPLE 18

11-(Trimethylammonio)undecanoylated polystyrene chloride (Example 7b) (11.1 g) was treated with sodium borohydride (3.8 g) in IMS (200 ml) by the method described in Example 17. After work-up 1-hydroxy-11(trimethylammonio)undecanoylated polystyrene chloride was isolated as off-white polymer beads (10.63 g) (1.74 meq Cl−/g).

EXAMPLE A

A liquid formulation for oral administration is prepared from the following:

|  | (w:v) |
|---|---|
| Compound of Structure (I) | 10% |
| Avicel RC591 | 1.25% |
| Antifoam emulsion | 0.05% |
| Flavours | 0.02% |
| Sodium saccharide | 0.01% |
| Preservatives: |  |
| Methyl Parabenz | 0.12% |
| Propyl Parabenz | 0.04% |
| Sorbitol syrup (70%) | 30% |
| Glycerin | 5% |
| Water | to 100% |

EXAMPLE B

A capsule formulation for oral administration is prepared by incorporating the following into a soft gelatin capsule:

Compound of Structure (I) (500 mg), Aerosil 200 (5 mg), Magnesium Stearate (5 mg), Avicel PH101 (40 mg), and, optionally, sodium starch glycollate (10 mg).

EXAMPLE C

A food additive formulation for example a sachet for reconstitution or mixing with food, is prepared by incorporating into a powder formulation, compound of Structure (I) (2500 mg), sodium carboxymethylcellulose (50 mg), sucrose (2400 mg) and flavours (50 mg).

DATA

Bile Acid Binding assay

Test compound (150 mg) was equilibrated with 5 mM sodium glycocholate (30 ml)—a typical physiological concentration—in Krebs' buffer for 3 hours. The compound was separated by centrifugation and the total bound determined by subtraction of the amount in the supernatant from the total bile acid used. Bile acid dissociation was measured by resuspending the compound in Krebs' buffer, shaking and sampling the mixture through a filter at several time points up to 20 minutes. Radioactivity and hence bile acid dissociated was determined in the filtrate (Table I).

TABLE I

| Example No. | GC Bound mmoles/g | | % Dissociated |
|---|---|---|---|
|  | t = 0 | t = 2 minutes |  |
| 1 | 0.88 | 0.74 | 16 |
| 2 | 0.87 | 0.71 | 18 |
| 3 | 0.83 | 0.78 | 6 |
| 4 | 0.87 | 0.78 | 10 |
| 5 | 0.88 | 0.79 | 10 |
| 6 | 0.78 | 0.65 | 17 |
| 8 | 0.89 | 0.77 | 12 |
| 9 | 0.92 | 0.85 | 8 |
| 10 | 0.79 | 0.66 | 17 |
| 11 | 0.81 | 0.68 | 16 |
| 12 | 0.90 | 0.82 | 9 |
| 13 | 0.87 | 0.79 | 9 |
| 14 | 0.96 | 0.93 | 3 |
| 15 | 0.80 | 0.65 | 19 |
| 16 | 0.83 | 0.69 | 17 |
| 17 | 0.84 | 0.66 | 21 |
| 18 | 0.78 | 0.69 | 12 |
| Cholestyramine | 0.75 | 0.50 | 33 |

What is claimed is:

1. A polystyrene polymer of structure (I)

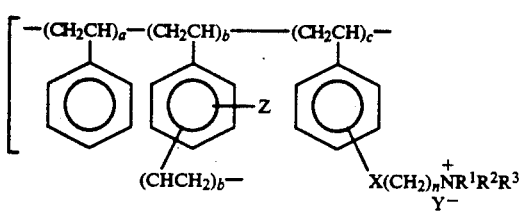

in which,

X is $CH_2$, CO or CHOH;

Z is H or a group $X(CH_2)_nN^+R^1R^2R^3$;

n is 2 to 15;

$R^1$ and $R^2$ are the same or different and are each $C_{1-4}$alkyl;

$R^3$ is $C_{1-20}$alkyl; or $R^1$, $R^2$ and $R^3$ together with the nitrogen atom to which they are attached form a ring, optionally containing one or more further heteroatoms, and optionally being substituted with a $C_{1-4}$alkyl group;

a, b and c are numbers which indicate the relative molar percentages of the units present in a random distribution in said polymer, (b) being from about 0.5 to about 10 molar percent, and (c) being from about 30 to about 99 molar percent;

m is a number indicating the degree of polymerisation of said polymer, and $Y^-$ is a physiologically acceptable counter ion;

2. A polystyrene polymer as claimed in claim 1 in which X is $CH_2$ and $R^1$ to $R^3$ are each methyl.

3. A polystyrene polymer as claimed in claim 2 in which (b) is from about 1 to about 4 molar percent of said polymer.

4. A polystyrene polymer as claimed in claim 1 which is
6-(N,N-dimethyl-N-octylammonio)hexanoylated polystyrene chloride.

5. A polystyrene polymer as claimed in claim 1 which is
6-(N,N-dimethyl-N-dodecylammonio)hexanoylated polystyrene chloride.

6. A polystyrene polymer as claimed in claim 1 which is
11-(trimethylammonio)undecanoylated polystyrene chloride.

7. A polystyrene polymer as claimed in claim 1 which is 11-(trimethylammonio)undecylated polystyrene chloride.

8. A polystyrene polymer as claimed in claim 1 which is
11-(trimethylammonio)undecanoylated polystyrene chloride.

9. A polystyrene polymer as claimed in claim 1 which is
11-(1-pyridino)undecanoylaed polystyrene chloride.

10. A polystyrene polymer as claimed in claim 1 which is
8-(trimethylammonio)octanoylated polystyrene chloride.

11. A polystyrene polymer of structure (II)

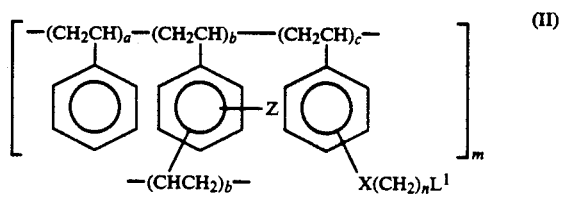

in which X, Z, n, a, b, c and m are as described for structure (I) in claim 1 and $L^1$ is a group displaceable by an amine.

12. A polystyrene polymer of structure (IV)

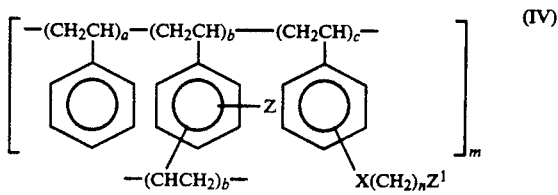

in which Z, X, n, a, b, c and m are as described for structure (I) and $Z^1$ is $NR^1R^2$ or $NR^2R^3$ in which $R^1$ to $R^3$ are as described for structure (I) in claim 1.

* * * * *